(12) United States Patent
Fernfors

(10) Patent No.: US 8,251,968 B2
(45) Date of Patent: Aug. 28, 2012

(54) ABSORBENT ARTICLE WITH A CHECKING FUNCTION FOR ELASTIC ELONGATION

(75) Inventor: Ingemar Fernfors, Molndal (SE)

(73) Assignee: SCA Hygiene Products AB, Göteborg (SE)

( * ) Notice: Subject to any disclaimer, the term of this patent is extended or adjusted under 35 U.S.C. 154(b) by 776 days.

(21) Appl. No.: 11/762,949

(22) Filed: Jun. 14, 2007

(65) Prior Publication Data

US 2009/0292269 A9 Nov. 26, 2009

Related U.S. Application Data

(63) Continuation of application No. PCT/SE2004/001863, filed on Dec. 14, 2004.

(51) Int. Cl.
*A61F 13/15* (2006.01)
*A61F 13/20* (2006.01)

(52) U.S. Cl. ........................................ 604/386; 604/389

(58) Field of Classification Search .................. 604/361, 604/385.01, 385.24–385.3, 391–396
See application file for complete search history.

(56) References Cited

U.S. PATENT DOCUMENTS

| | | | | |
|---|---|---|---|---|
| 3,613,679 | A * | 10/1971 | Bijou | 602/75 |
| 4,807,640 | A * | 2/1989 | Watson et al. | 600/534 |
| 4,958,853 | A * | 9/1990 | Doty | 280/801.1 |
| H0001674 | H * | 8/1997 | Ames et al. | 604/389 |
| 5,957,908 | A * | 9/1999 | Kline et al. | 604/386 |
| 6,142,968 | A * | 11/2000 | Pigg et al. | 602/75 |
| 6,228,804 | B1 * | 5/2001 | Nakashima | 503/226 |
| 6,558,499 | B1 * | 5/2003 | Pargass et al. | 156/250 |
| 6,671,884 | B1 * | 1/2004 | Griesbach, III | 2/69 |
| 6,820,478 | B1 * | 11/2004 | Nabarro et al. | 73/149 |
| 7,347,845 | B2 * | 3/2008 | Zajaczkowski | 604/385.01 |
| 7,422,256 | B2 * | 9/2008 | Mueller | 294/74 |
| 2003/0144596 | A1 * | 7/2003 | Tsubata | 600/500 |
| 2005/0143699 | A1 * | 6/2005 | Linder | 604/383 |
| 2005/0256479 | A1 * | 11/2005 | Carlucci et al. | 604/385.01 |
| 2006/0068168 | A1 * | 3/2006 | Olson et al. | 428/152 |

FOREIGN PATENT DOCUMENTS

GB 2 267 024 11/1993

(Continued)

OTHER PUBLICATIONS

Stedman's Medical Dictionary, 27th ed., definition of "bandage".*

(Continued)

*Primary Examiner* — Melanie Hand
(74) *Attorney, Agent, or Firm* — Buchanan Ingersoll & Rooney PC

(57) ABSTRACT

An absorbent article includes at least one elastic area. The article contains an element for checking the elongation of the elastic area, in conjunction with which a first indicator marker is connected to the elastic area and a second indicator marker is connected to a second piece of material. The first indicator marker and the second indicator marker are capable of displacement relative to one another in the direction of elongation of the elastic area, whereby the change in the relative position between the first and the second indicator marker in conjunction with the elongation of the elastic area from a non-elongated position provides a measure of the elongation of the elastic area.

24 Claims, 6 Drawing Sheets

FOREIGN PATENT DOCUMENTS

| | | | |
|---|---|---|---|
| GB | 2267024 A | * | 11/1993 |
| JP | 63-019505 U | | 2/1988 |
| JP | 05-317356 | | 12/1993 |
| JP | 06-011725 U | | 2/1994 |
| JP | 2000-060899 | | 2/2000 |
| JP | 2004-305600 | | 11/2004 |
| WO | WO 9851247 A1 | * | 11/1998 |
| WO | 03/022730 | | 3/2003 |
| WO | 2005/053588 | | 6/2005 |

OTHER PUBLICATIONS

Definition of "clothing", Websters Third New International Dictionary, unabridged.*

Definintion of "diaper", Websters Third New International Dictionary, unabridged.*

An English Translation of the Notice of Reasons for Rejection issued in the corresponding Japanese Patent Application No. 2007-546593 dated Jan. 26, 2010.

* cited by examiner

ABSORBENT ARTICLE WITH A CHECKING FUNCTION FOR ELASTIC ELONGATION

BACKGROUND

1. Technical Field

The invention relates to an absorbent article comprising at least one elastic area.

2. Description of Related Art

In the case of absorbent articles such as diapers, sanitary towels, incontinence guards, etc., the arrangement of elastic areas executed in various ways is previously disclosed.

It is common, for example, for the elastic areas to be arranged by having provided the article with elastic threads or elastic tapes which have been attached, for example, in their stretched state to the covering layer of the article.

The elastic areas are often so arranged that they tighten the article around the wearer's legs, around the wearer's waist or the like.

For certain articles, it is also the case that entire surfaces consist of elastic areas. Articles are encountered, for example, with elastic covering layers arranged on the side of the article that is intended to face away from the wearer when the article is being worn.

Elastic areas which tighten the article around the wearer's legs are described, for example, in U.S. Pat. No. 3,860,003.

Elastic areas are also described in a number of different patent specifications, in which the elastic areas are arranged in the waist area of the article. One example of such a document is WO 93/17648.

Attachment flaps intended to secure the article around the wearer's waist in conjunction with putting on the article are another application which usually contains elastic material, in conjunction with which at least a part of the length of the attachment flap is elastic. One example of such attachment flaps is described in U.S. Pat. No. 5,916,207.

A disadvantage associated with all previously disclosed articles comprising some form of elastic areas is the existence of a significant risk of the elastic areas being stretched too tightly around the wearer, as a consequence of which skin irritations, blood circulation problems or the like can occur.

For example, an article that is too small can be secured around a wearer's waist by stretching the attachment flaps of the article too far, as a consequence of which the waist area of the entire article is tensioned excessively tightly around the wearer's waist.

Another commonly encountered problem is that the leg elastic of absorbent articles surrounds the wearer's legs too tightly, as a consequence of which the leg elastic cuts into the wearer's groin, which often results in red marks, chafing or some other form of skin irritation.

Excessive pressure against the body combined with an article which contains urine and/or feces is a particularly undesirable combination, which is unfortunately very common in connection with absorbent articles. The combination increases the risk of skin irritations to a significant degree.

Another problem associated with the use of absorbent articles containing elastic areas is that the elastic is not tensioned sufficiently tightly. A commonly encountered situation, for example, is that parents do not tension the diaper sufficiently tightly around their infant, which is a particularly commonly encountered situation for as long as the infant retains its umbilical cord. A diaper that is too loosely tensioned often results in the unnecessary leakage of urine and/or feces.

SUMMARY

The need accordingly exists for absorbent articles in which it is possible to check that the tension in the elastic areas of the article lies within intended limits and is not too tight or too loose.

An absorbent article of the kind mentioned in the introduction has been achieved herein, however, which essentially overcomes the problems that have been associated with previously disclosed absorbent articles.

An absorbent article in accordance with an embodiment of the disclosed herein comprises means for checking the elongation of the elastic area. For this purpose, the means comprises a first indicator marker connected to the elastic area and a second indicator marker connected to another piece of material. The first indicator marker and the second indicator marker are capable of displacement relative to one another in the direction of elongation of the elastic area, whereby the change in the relative position between the first and the second indicator markers in conjunction with the elongation of the elastic area from a non-elongated position provides a measure of the elongation of the elastic area.

In accordance with a first embodiment, the first indicator marker is displaced in the direction of elongation when the elastic area is elongated, as a consequence of which it is displaced over a longer distance than the second indicator marker.

In accordance with a second embodiment, the mutual distance between the first indicator marker and the second indicator marker reduces in conjunction with the initial elongation of the elastic area.

In accordance with a third embodiment, the second piece of material which comprises the second indicator marker is attached to the elastic area along a connecting line essentially perpendicular to the direction of elongation of the elastic area. The second indicator marker is arranged at a distance from the aforementioned attachment in the direction of elongation of the elastic area.

When the elastic area is elongated, there is no change in the distance between the perpendicular attachment and the second indicator marker that is arranged on the separate piece of material. The distance between the perpendicular attachment and the first indicator marker changes, on the other hand, when the elastic area between the connection and the first indicator marker is elongated.

In accordance with one embodiment of the invention, the second indicator marker consists of one edge of the second piece of material. The edge is arranged at a distance from the connecting line of the piece of material and is essentially perpendicular to the direction of elongation of the elastic area.

In accordance with another embodiment, the first indicator marker is concealed under the second piece of material when the elastic area is not stretched. An absorbent article in accordance with this embodiment conveniently indicates when the elastic area of the article has been stretched too much. The first indicator marker is conveniently concealed under the separate piece of material containing the second indicator marker. The second indicator marker appropriately consists of the edge of the piece of material that is arranged at a distance from the attachment between the piece of material and the absorbent article, in conjunction with which the first indicator marker appears at the aforementioned edge when the elastic area has been stretched too much.

In accordance with a further embodiment, the first indicator marker comprises at least two indicator levels, in conjunction with which at least one indicator level indicates that the elastic area has been stretched too much. It is appropriate, for example, for the first indicator marker to exhibit a first level, which indicates that the elastic area of the article has been stretched sufficiently, and a second level, which indicates that the elastic area has been stretched too much.

One embodiment comprises at least one indicator level, which indicates that the elastic area of the article is not sufficiently stretched to ensure the satisfactory function of the article.

Insufficient stretching of elastic areas of absorbent articles is not altogether a rare occurrence, which can result in failure by the article to achieve its intended function. The parents of newborn infants, for example, tend to be particularly concerned about stretching the waist area of the diaper to tightly over the umbilical cord. It is beneficial for this reason to be able to send a signal indicating that the article has not been tensioned in the intended fashion.

In accordance with one embodiment, the absorbent article consists of a panty diaper.

In accordance with one embodiment, the elastic area of the panty diaper consists of the waist elastic of the panty diaper.

One embodiment is characterized in that the absorbent article is an open, all-in-one diaper, and in accordance with one embodiment the elastic area consists of at least one part of at least one of the attachment flaps of the all-in-one diaper.

In accordance with one embodiment, the attachment flap is attached to the backing layer of the all-in-one diaper between the longitudinal edge and the longitudinal center line of the diaper, in conjunction with which the first indicator marker is arranged on the attachment flap. The first indicator marker is arranged in this case between the attachment and the longitudinal edge, in conjunction with which at least one part of the attachment flap between the attachment and the first indicator marker is elastic. The second indicator marker is arranged on the backing layer and positioned in the transverse direction of the article between the first indicator marker and the longitudinal edge of the all-in-one diaper, in conjunction with which the backing layer constitutes the second piece of material.

In accordance with one embodiment, the second indicator marker consists of the longitudinal edge of the all-in-one diaper.

In accordance with one embodiment, at least one part of the extent of the attachment flap between its attachment to the backing layer and the longitudinal edge of the all-in-one diaper is concealed under a piece of material.

In accordance with one embodiment, the piece of material forms a pocket together with the backing layer, in conjunction with which the pocket is open where the attachment flap extends outwards from the pocket, and in conjunction with which the attachment between the attachment flap and the backing layer is arranged inside the pocket.

In one embodiment, the elastic area consists of the waist elastic of the all-in-one diaper.

One embodiment is characterized in that the absorbent article is the so-called belt diaper.

At least one part of at least one of the belt halves of the belt diaper constitutes the elastic area in one embodiment.

In one embodiment, the belt half is attached to the backing layer of the belt diaper between the longitudinal edge and the longitudinal center line of the diaper. The first indicator marker is arranged in this case on the belt half between the connection and the longitudinal edge, in conjunction with which at least one part of the belt half between the attachment and the first indicator marker is elastic. The second indicator marker is arranged on the backing layer and positioned in the transverse direction of the article between the first indicator marker and the longitudinal edge, in conjunction with which the second piece of material consists of the backing layer.

In accordance with one embodiment, the second indicator marker consists of the longitudinal edge of the belt diaper.

In one embodiment, the halves of the belt are arranged between the liquid-permeable covering layer and the backing layer.

In another embodiment, at least one part of the extent of the belt half between its attachment to the backing layer and the longitudinal edge of the belt diaper is concealed under a piece of material.

In accordance with one embodiment, the piece of material forms a pocket together with the backing layer, in conjunction with which the pocket is open where the belt half extends outwards from the pocket, and in conjunction with which the attachment between the belt half and the backing layer is arranged inside the pocket.

DESCRIPTION OF THE ILLUSTRATIVE EMBODIMENTS

Figure 1A:
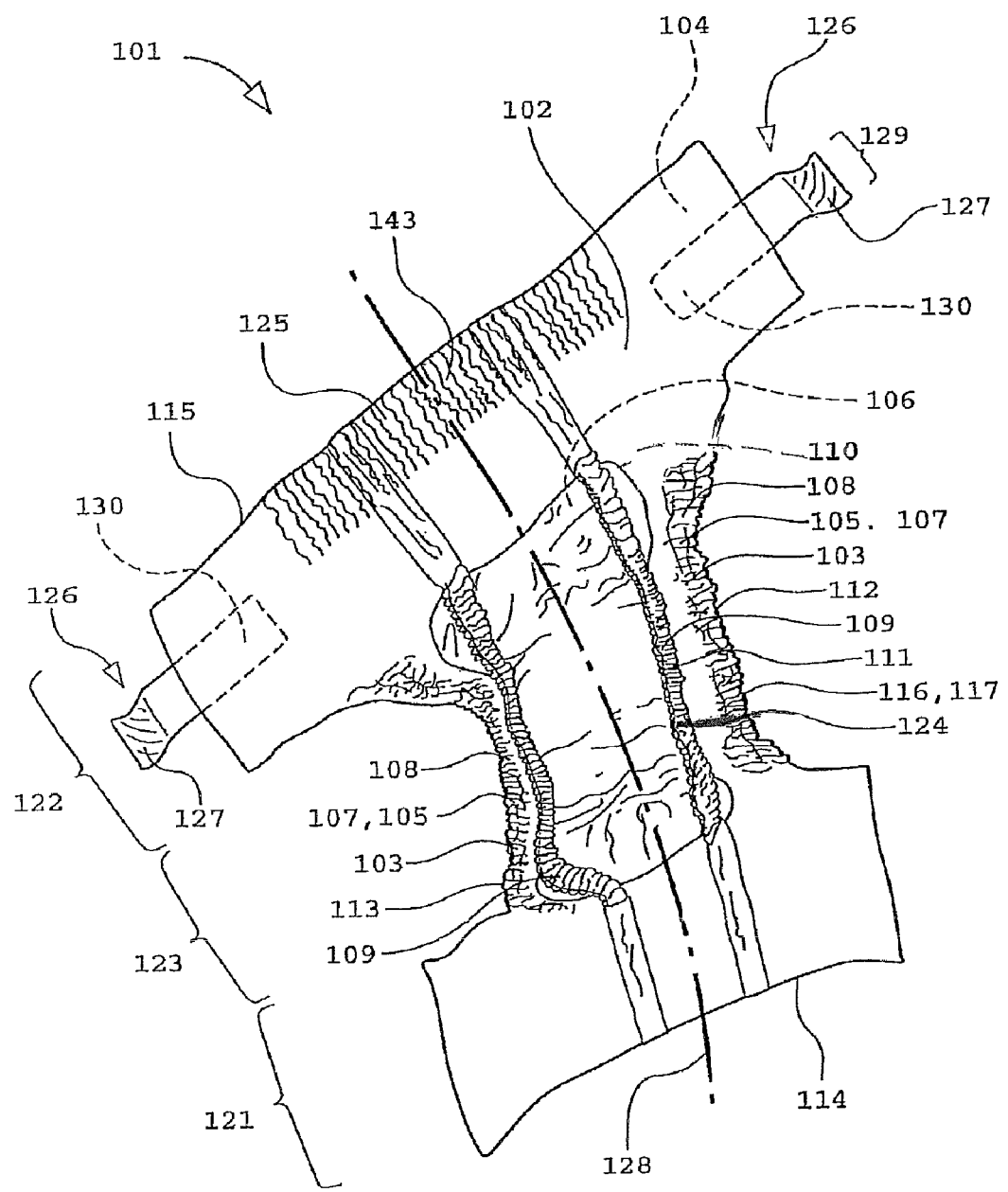
FIG. 1a shows an all-in-one diaper in accordance with the first preferred embodiment of the invention from the side that is intended to face towards the wearer when wearing the diaper.

One preferred embodiment of the invention is an absorbent article for disposable use comprising at least one elastic area, in conjunction with which the elastic area comprises means for checking the degree of extension of the area. It is a common occurrence, for example, for the article to have been tensioned too tightly or too loosely around the waist of the wearer after it has been put on, which can be checked with the help of a means for checking the degree of elongation of the waist elastic or the elastic attachment tabs of the article.

Absorbent articles in accordance with the invention primarily denotes absorbent articles of the type all-in-one diapers, panty diapers, belt diapers or sanitary protection of the panty type, that is to say articles which enclose the wearer's abdomen when they are being worn and which usually comprise one or more elastic areas.

It is naturally also possible to apply the invention to less absorbent products such as sanitary towels, panty liners or light incontinence guards intended to be positioned in the crotch of a wearer. The design and positioning of these articles in a wearer's undergarments means, however, that the need for indication of elongation is not as beneficial for these types of absorbent articles.

All-in-one diapers, panty diapers or belt diapers may consist of baby's diapers intended for infants who are not yet potty trained, or of incontinence guards intended for adult incontinent wearers.

So-called panty diapers are characterized above all in that they have already been folded at the time of manufacture about an essentially transverse fold line in the crotch area of the panty diaper and have subsequently been joined together at the waist. Diapers of this type are intended to be put on a wearer precisely like a pair of underpants, that is to say they are passed over the wearer's legs. The joint in the waist area of the panty diaper is usually capable of separation, as a consequence of which the panty diaper can be removed after use without having to be passed all the way down over the wearer's feet when it is to be removed. This possibility is particularly appreciated when the panty diaper is smeared with feces after use. Panty diapers normally comprise elastic areas both in the waist part and around the leg openings.

Panty diapers that are capable of being opened and reclosed also exist.

Such panty diapers are supplied joined together at the waist, although they can be opened, for example to check the contents of the article, and then reclosed.

Belt diapers are characterized in that they comprise a transverse belt in relation to the absorbent part of the diaper, which belt is attached to either the front or the rear transverse edge of the diaper.

When putting on a belt diaper of this kind, the belt is fixed around the wearer's waist as a first stage. The absorbent part of the diaper thus hangs loosely from the belt. The absorbent part of the diaper is then passed between the wearer's legs and is attached to the belt, in conjunction with which the belt includes fixing surfaces intended to adhere strongly to fixing devices arranged on the absorbent part of the diaper adjacent to its free transverse edge. The belt and the leg cut-outs are usually elasticated in panty diapers.

So-called all-in-one diapers are characterized in that they include attachment flaps, by means of which the front and rear waist part of the diaper are attached when the diaper is applied around the waist of a wearer. All-in-one diapers usually comprise elastic areas next to the leg cut-outs and in conjunction with the waist area where at least parts of the waist part usually contain elastic devices. The attachment flaps contain elastic areas in many all-in-one diapers.

FIG. 1a shows essential components of a diaper 101 in accordance with the first preferred embodiment of the invention.

The diaper 101 is an open diaper of the so-called all-in-one type. The diaper 101 is not joined together at the waist area when it is sold, but is instead intended to be applied around a wearer's abdomen, in order thereafter to be joined together around the wearer's waist. This type of diaper 101 is commonly encountered for both infant and adult incontinent wearers.

The diaper 101 is essentially in the form of an hourglass and as such exhibits longitudinal edges 112, 113, a front transverse edge 114 and a rear transverse edge 115. The diaper 101 also exhibits a front end part 121, a rear end part 122 and a narrower crotch part 123 situated between the end parts 121, 122. The crotch part 123 is intended to be situated in the narrowest area between the wearer's thighs when it is being worn.

When wearing the diaper 101, the front part of the crotch part 123 and the front end part 121 function principally as a receiving area for urine, while the rear part of the crotch part 123 and the rear end part 122 function principally as a receiving area for feces.

The diaper 101 comprises a liquid-permeable covering layer 102 arranged over the surface of the diaper 101 that is intended to face towards the wearer when it is being worn, a backing layer 104 arranged over the surface of the diaper that is intended to face away from the wearer when it is being worn, an absorption body 106 enclosed between the liquid-permeable covering layer 102 and the backing layer 104, and side flaps 103 arranged outside the absorption body 106.

The liquid-permeable covering layer 102 of the diaper 101 extends outside the absorption body 106 around the entire periphery of the absorption body 106. The liquid-permeable covering layer 102 can consist of any material that is suitable for the purpose. Examples of commonly encountered liquid-permeable covering materials are non-woven textile materials, known as nonwoven materials, perforated plastic films, meshes made of plastic or textile, and liquid-permeable foam layers. Liquid-permeable covering materials that are made of continuous thin fibers, which extend predominantly in the longitudinal or transverse direction of the article, are also encountered. Laminates consisting of two or more of the above-mentioned possible covering materials are also commonly encountered, as are coverings consisting of different materials in different parts of the surface.

A situation commonly encountered today is that the liquid-permeable covering layer 102 consists of a fully or partially elastic material in order to provide the diaper 101 with a better fit when it is being worn.

Diapers 101 containing absorption bodies 106 which exhibit especially high strength and resistance to wear may even function without the need to provide any extra liquid-permeable covering layer on that side of the diaper 101 that faces towards the wearer when it is being worn.

The backing layer 104 also extends beyond the absorption body 106 around the entire periphery of the absorption body 106. Backing layers 104 that are normally present on diapers 101 are usually liquid-impermeable, although other types of backing layer are also encountered. The backing layer 104 can consist of a range of different materials. The backing layer 104 most commonly consists of a thin, liquid-tight plastic film, although it is also possible to use other types of liquid-tight material, such as nonwoven materials that have been made liquid-tight for example by means of plastic coating, liquid-tight foam layers, liquid-tight adhesive or similar. The backing layer 104 can also consist of a liquid-tight, vapor-permeable material. Also encountered are laminates containing at least one liquid-tight layer arranged against the absorption body 106. These laminates usually consist of a liquid-tight material functioning as a moisture barrier and a more textile-like material arranged on the side of the diaper 101 that faces away from the wearer when it is being worn, as a consequence of which the outside of the diaper 101 more closely resembles an item of clothing when it is being worn. The textile-like layer of the laminate usually consists of a nonwoven layer, in conjunction with which the nonwoven layer can be executed so that it functions as a receiving material for a Velcro® material of the male type. A nonwoven material of this kind is characterized in that it comprises closed eyes, so-called loops, or the like.

The liquid-permeable covering layer 102 and the backing layer 104 are attached to one another outside the absorption body 106 along the entire periphery of the absorption body 106.

The liquid-permeable covering layer 102 and the backing layer 104 may be attached to one another by a number of different means. Examples of means of attachment include gluing, thermal fusion, ultrasonic welding or the like.

Elastic devices 105 are arranged outside the absorption body 106 in those parts of the side flaps 103 of the diaper 101 which run essentially in the longitudinal direction of the diaper 101. The elastic devices 105 function as leg elastic and have the task of preventing liquid and feces from leaking out past the longitudinal edges 112, 113 of the diaper 101, and in this way they form outer moisture barriers 108 together with surrounding layers. The elastic devices 105 consist of one or more elastic threads that have been applied in their stretched state between the liquid-permeable covering layer 102 and the backing layer 104, at least in the crotch part 123 of the diaper 101. The elastic devices 105 are attached to the backing layer 104 and the covering layer 102 by gluing, ultrasonic welding or the like. The leg elastic is an example of the elastic areas 107 of the diaper 101.

In alternative embodiments, the elastic devices can be arranged on the side of the side flaps 103 that is intended to face towards the wearer when it is being worn, or on the opposite side of the side flaps, and as such they are naturally only attached to the covering layer 102 and the backing layer 104 respectively.

The elastic devices can, in alternative embodiments, consist of elastic tape material, for example made of a foam material.

The hourglass-shaped absorption body 106 can be constructed from one or more layers of cellulose fluff pulp. The cellulose fluff pulp can be mixed for this purpose with fibers or particles of a high-absorbency polymer material of the kind which, in conjunction with absorption, chemically bonds large quantities of liquid to form a liquid-containing gel. The absorption body 106 can also contain high-absorbency polymer material arranged in a layer inside the absorption body or in conjunction with the surface or surfaces of the absorption body. Additional components to improve the characteristics of the absorption body 106 can also be present in the absorption body 106. Examples of such components include binding fibers, different types of liquid-distributing layers or fibers, form-stabilizing components, reinforcing fibers or the like. The absorption body 106 can naturally also consist of other types of absorption material, such as absorbent nonwoven material, absorbent foam, textile materials, peat or mixtures of different kinds of absorption material.

It is a customary occurrence for the absorption body 106 to be created in conjunction with the manufacture of the diaper, in conjunction with which the different components of the absorption body 106 are mixed and layered in an appropriate fashion in the production machine. Also encountered are absorption bodies that have been manufactured on separate production lines not connected to the machine which manufactures the diapers. Prefabricated absorption material is usually supplied in roll form, in conjunction with which the material is cut and folded to the stipulated configuration in the machine for the manufacture of diapers. Prefabricated absorption material can contain the same components as absorption bodies manufactured directly in the production machine for diapers. Binding fibers are in principle a necessary component in prefabricated absorption material in order for these to be capable of being handled in a simple fashion.

Special layers with the ability rapidly to receive quite large quantities of liquid and to retain this liquid temporarily, in order subsequently to release the temporarily stored liquid to other parts of the absorption body 106, can also be included in diapers of the prescribed kind. Such receiving layers are normally arranged for this purpose between the liquid-permeable covering layer 102 of the diaper 101 and the absorption body 106. No receiving layer is shown in FIG. 1a.

In order further to prevent liquid or feces from leaking out via the side edges 112, 113 of the diaper 101, the diaper 101 is provided with inner side leakage barriers 109 on the side that is intended to face towards the wearer when it is being worn. The inner side leakage barriers 109 are arranged adjacent to the longitudinal edges 110 of the absorption body 106 and extend essentially in the longitudinal direction of the diaper 101. The respective inner side leakage barrier 109 is executed from a separate material strip 111, which exhibits two essentially parallel longitudinal edges 116, 117. The material strip 111 is double-folded, in conjunction with which the longitudinal edges 116, 117 of the material strip 111 are arranged adjacent to one another. The edges 116, 117 of the material strip 111 are attached to the covering layer 102 and constitute the attached edge of the inner side leakage barrier. The folded edge of the material strip 111 constitutes the free edge of the inner side leakage barrier 109.

The inner side leakage barriers 109 are folded down and attached to the covering layer 102 on the front end part 121 and the rear end part 122 of the diaper 101.

The inner side leakage barriers 109 comprise elastic elements 124 attached to the inner side leakage barriers 109 in their pre-tensioned state. The elastic elements 124 are conveniently arranged adjacent to the free edges of the inner side leakage barriers 109. When the pre-tensioned elastic elements 124 are released, they contract together with the free edges of the inner side leakage barriers 109, thereby causing the inner side leakage barriers 109 to be brought into a raised configuration remote from the liquid-permeable covering layer 102, at least, in the crotch part 123 of the diaper 101, where the side leakage barriers 109 are not folded down and attached to the covering layer 102.

The rear and/or front parts of the diaper 101 can also be provided with so-called waist elastic 125, which consists of elastic devices arranged along the front transverse edge 114 and/or the rear transverse edge 115 of the diaper 101 in order to provide the diaper 101 with a soft and pliable closure around the wearer's waist. In the illustrative embodiment described here, only the rear end part 122 of the diaper 101 is provided with waist elastic 125. The waist elastic 125 consists of a thin strip of elastic foam material, which is attached by means of adhesive between the backing layer 104 and the liquid-permeable surface layer 102. The waist elastic 125 is applied in its stretched state between the layers 102, 104 in order to bring about a holding force which stretches the diaper 101 around the wearer's waist.

The waist elastic 125 constitutes one of the elastic areas 143 of the diaper 101.

Two soft and elastic attachment flaps 126 are arranged on the rear end part 122 for the purpose of securing the diaper 101 around a wearer. One attachment flap 126 is arranged for this purpose on each side part of the rear end part 122. The attachment flaps 126 connect the rear end part 122 to the front end part 121 when it is being worn by the attachment flaps 126 exhibiting fixing devices 127, which can be attached to a receiving part arranged on the front end part 121 of the diaper 101. The attachment flaps 126 are executed from a very soft material, for example from a single, elastic nonwoven layer or a soft elastic laminate.

In alternative embodiments, it is possible to envisage that only a part of the length of the attachment flap is elastic.

The elastic attachment flaps 126 constitute a further example of elastic areas 144 in the diaper 101.

The fixing devices 127 preferably consist of male parts of a Velcro® material and are attached to the attachment flaps 126, for example with adhesive, on the side of the attachment flaps 126 which faces towards the receiving part when the diaper 101 is being worn.

The receiving part, which is not shown in FIG. 1a, for the attachment flap 126 consists of a strip of a receiving material adapted for the fixing device 127 of the attachment flap 126. The receiving part extends essentially parallel to the front transverse edge 114 of the side of the diaper that faces away from the wearer when it is being worn, that is to say on the side of the backing layer 104 that faces away from the absorption body 106. In the illustrative embodiment described here, the material in the receiving part consists of a female part of a Velcro® material and is appropriately executed so that its extent in the longitudinal direction of the diaper 101 corresponds to the width 129 of the attachment flaps 126. The receiving part extends largely over the entire width of the diaper 101 in the transverse direction of the diaper 101.

In alternative illustrative embodiments of a diaper, it is possible to envisage the arrangement of separate receiving parts for the respective fixing devices 127, in which case the receiving parts are arranged adjacent to the longitudinal edges 112, 113 of the diaper on the front transverse edge 114 of the diaper 101.

When putting the diaper 101 on an infant, the diaper 101 is placed between the infant's legs in the infant's crotch. The diaper 101 is then closed around the infant's waist by causing the attachment flaps 126 to overlap the front end part 121 so that the fixing devices 127 of the attachment flaps 126 can be applied to the receiving part in order to hold the diaper securely in place.

The attachment flaps 126 are attached to the rear end part 122 in the attachment areas 130 that are positioned in those areas of the rear end part 122 which lie between the lateral edges 112, 113 running in the longitudinal direction and the longitudinal center line 128 of the diaper. The attachment areas 130 consist of parts of the attachment flaps 126 and those parts of the rear end part 122 that are attached to one another.

The fixing devices 127 of the attachment flaps 126 in alternative embodiments can consist of a pressure-sensitive adhesive, in which case the receiving part (not shown in FIG. 1a) consists of a material to which the selected pressure-sensitive adhesive of the fixing devices 127 can be attached so as to achieve the appropriate joint strength. Combinations of materials are usually selected so that the attachment between the fixing devices 127 and the receiving part can be opened and reclosed to allow the diaper 101 to be checked while it is being worn.

In other alternative embodiments, the backing layer 104 can be adapted in such a way as to interact with the fixing devices 127 of the attachment flaps 126, in which case no special receiving part is required.

Figure 1B:
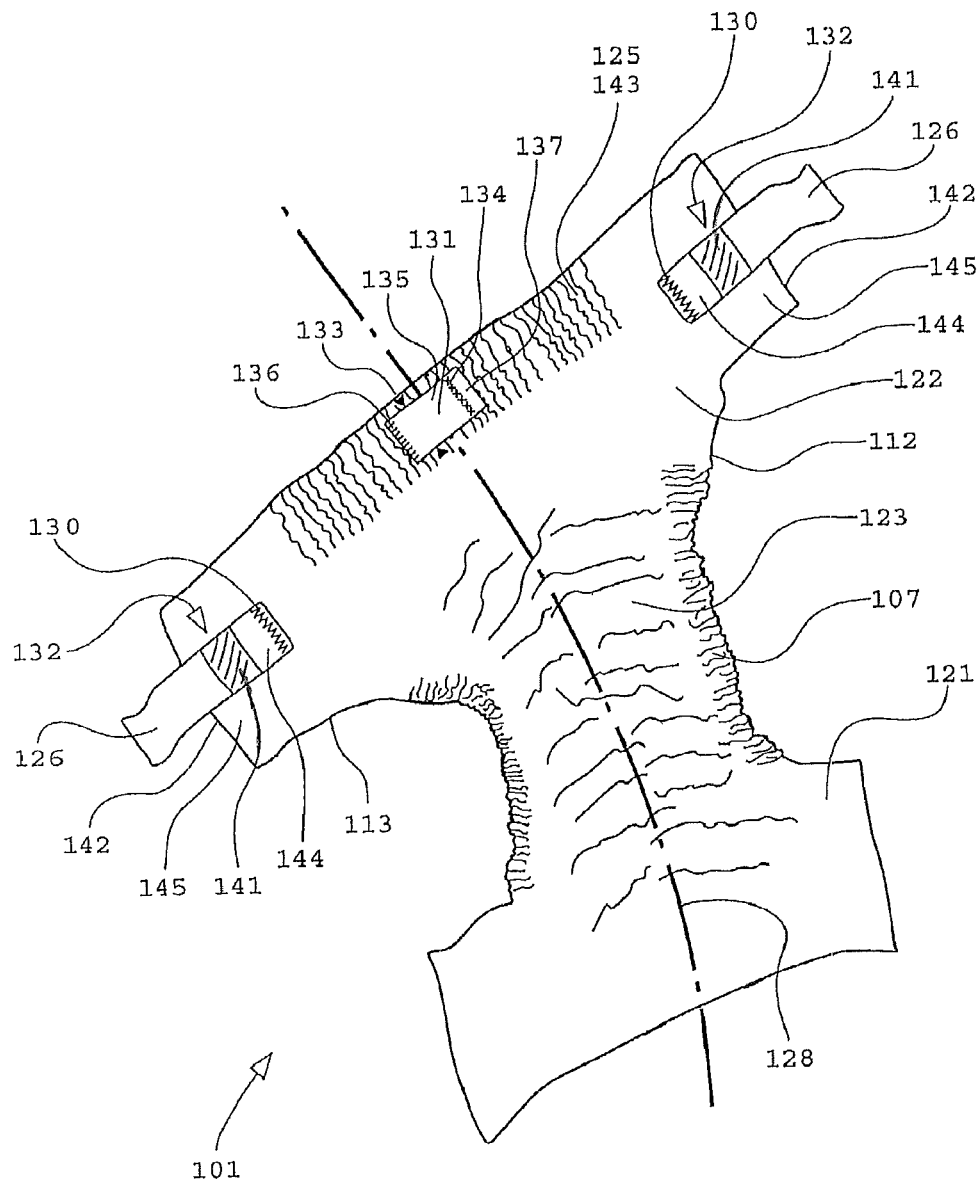
FIG. 1b shows the diaper in accordance with FIG. 1a from the side that is intended to face away from the wearer when wearing the diaper before it has been used.

The diaper 101 is shown in FIG. 1b from the side that is intended to face away from the wearer when it is being worn, in conjunction with which the diaper 101 is shown in a state in which the waist elastic 125 of the diaper 101 and the attachment flaps 126 of the diaper are drawn together.

The diaper 101 is characterized first and foremost in that it comprises, on the one hand, means 131 for checking the elongation of the waist elastic 125 and, on the other hand, means 132 for checking the elongation of the attachment flaps 126.

Figure 1C:
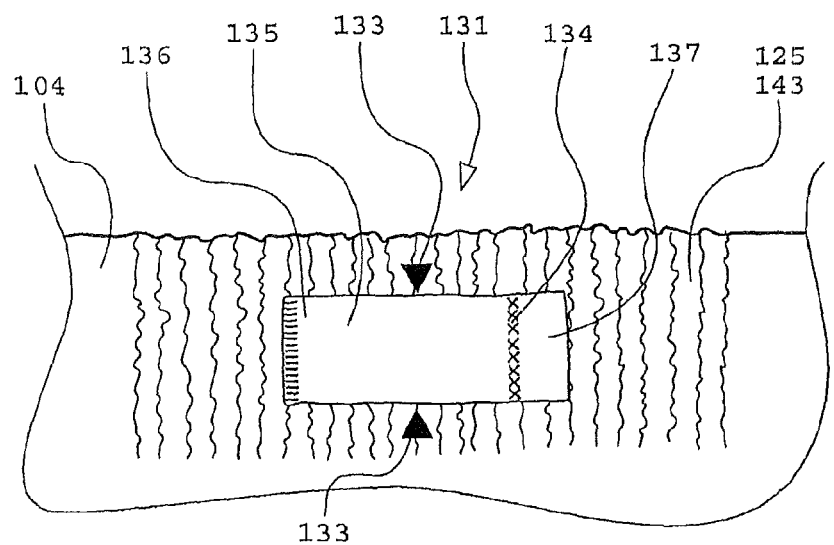
FIG. 1c is a schematic diagram that shows the waist elastic of a diaper with associated means for checking the elongation of the elastic when the elastic is in the contracted state.

Illustrated in FIG. 1c are the waist elastic 125 of the diaper 101 and the means 131 for checking the elongation of the elastic when the waist elastic 125 is in the contracted state.

Figure 1D:
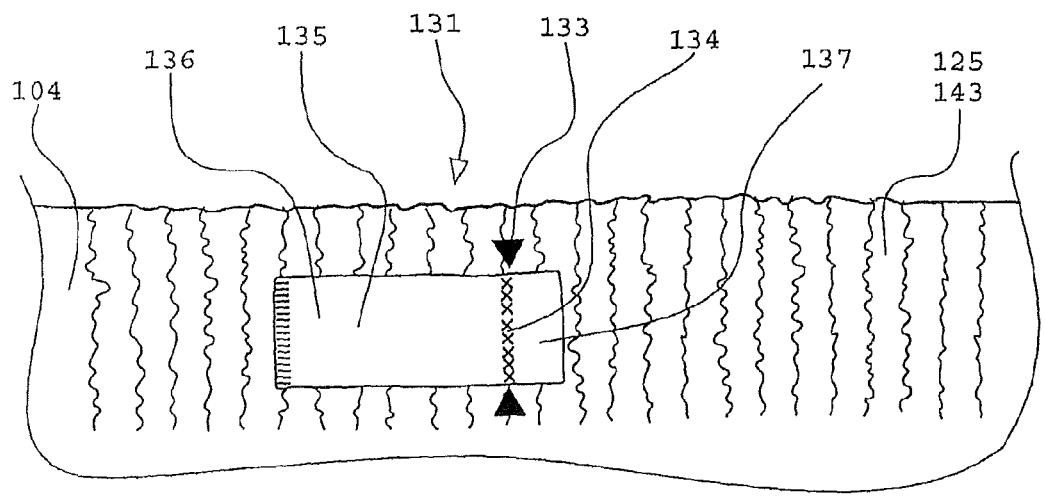
FIG. 1d is a schematic diagram that shows the waist elastic in FIG. 1c and the means for checking the elongation of the elastic in the stretched state.

FIG. 1d shows the waist elastic 125 and the means 131 for checking the elongation of the elastic when the waist elastic 125 has been elongated.

The means 131 for checking the elongation of the waist elastic 125 is arranged on the backing layer 104 of the diaper 101, as a consequence of which a check can be performed easily when the diaper 101 is being worn by a wearer. The means 131 is arranged on the waist elastic 125, in conjunction with which it is positioned essentially centrally on the elastic area both in the longitudinal direction and across the width of the waist elastic 125.

The means 131 consists of a first indicator marker 133 arranged on the waist elastic 125 and a second indicator marker 134 arranged on an essentially inelastic piece of material 135. In the embodiment described here, the essentially inelastic piece of material 135 is arranged on the waist elastic 125.

In alternative embodiments, the second indicator marker can be arranged on some other essentially inelastic part of the absorbent article.

The first indicator marker 133 in the illustrative embodiment described here consists of two triangles positioned adjacent to opposing longitudinal edges on the essentially inelastic piece of material 135. The triangles are visible to the side of the piece of material 135, in conjunction with which they are arranged opposite one another, each with its triangle tip pointing towards the piece of material 135. The triangles are arranged by means of appropriate printing technology on the backing layer 104, in conjunction with which they can exhibit an appropriate color.

In alternative embodiments, the first indicator marker 133 can consist of some other clearly visible marking arranged on the waist elastic 125. The use of lines, squares, figures or the like is as conceivable here as the triangles that constitute the first indicator marker 133 in the described embodiment.

The first indicator marker 133 naturally need not be arranged by means of printing technology, but may consists of, for example, a material resembling a label, which has been attached in an appropriate fashion to the backing layer or some other suitable alternative.

It is also possible to envisage the arrangement of the first indicator marker 133 between the backing layer 102 and the liquid-permeable covering layer 102 of the diaper 101, although this would require the indicator marker 133 to consist of a quite distinct color, and the backing layer 104 to exhibit a certain degree of transparency.

To sum up, it can be stated that the most important consideration is for the indicator marker 133 to be clearly visible when the diaper 101 is put on a wearer.

The first indicator marker 133 in other alternative embodiments can consist of, for example, a continuous line, which extends essentially across the longitudinal direction of the waist elastic 125, in conjunction with which the line extends outside the separate, inelastic piece of material 135. An indicator marker 133 of this kind is consequently partially concealed under the essentially inelastic piece of material 135 and is partially visible to the side of the piece of material 135.

It is also possible to envisage that the essentially inelastic piece of material 135 comprising the second indicator marker 134 consists of an essentially transparent material, in conjunction with which the first indicator marker 133 is visible through the piece of material. In such an embodiment of the inelastic piece of material 135, the first indicator marker 133 in its entirety can be placed under the piece of material 135.

The second indicator marker 134 is, as described above, arranged on an essentially inelastic piece of material 135.

The piece of material 135 exhibits rectangular form, in conjunction with which its longitudinal extent is oriented in the direction of elongation of the waist elastic 125. The piece of material 135 exhibits a first end area 136 and a second end area 137.

The first end area 136 is attached to the backing layer 104, and the second end area 137 is not attached but is free.

The attachment can be arranged in a number of different ways, for example by means of gluing, thermal fusion, ultrasonic welding or the like.

The second indicator marker 134, which is arranged on the essentially inelastic piece of material 135, consists of a row of crosses extending across the longitudinal extent of the piece of material 135.

When the waist elastic 125 is in its contracted state, the second indicator marker 134 is present between the first indicator marker 133 and the end of the piece of material 135 that is situated next to the second end area 137.

When the waist elastic 125 is stretched by being extended, the distance between the attachment of the essentially inelastic piece of material 135 to the backing layer 104 increases next to the first end area 136 and the first indicator marker 133.

The distance between the aforementioned attachment and the second indicator marker 134 remains unchanged, on the other hand, because the piece of material 135 is essentially inelastic.

The essentially inelastic piece of material 135 in its entirety can, depending on the point at which it is applied to the waist elastic 125, be displaced in one or other direction, although this is not relevant in relation to the invention. The crucial consideration in relation to the invention is that one distance increases (the waist elastic 125), while a second distance remains unchanged (on the essentially inelastic piece of material 135). The result is that the first indicator marker 133 moves closer to the second indicator marker (134), and when the two indicator markers 133,134 are situated adjacent to one another, as shown in FIG. 1d, the waist elastic 125 has reached the degree of elongation that should not be exceeded when wearing the diaper 101. If the first indicator marker 133 has passed the second indicator marker 134, the waist elastic 125 is tensioned too tightly, as a consequence of which the wearer may be affected adversely by the waist elastic 125 that is tensioned too tightly.

In alternative embodiments, one or other of the indicator markers 133,134 may exhibit an extent in the direction of elongation of the waist elastic 125, in conjunction with which an interval can be indicated, for example.

It is also possible to envisage that one or other of the indicator markers 133,134 exhibits a number of levels, in conjunction with which, for example, a first level indicates too little elongation/tensioning, a second level indicates correct elongation/tensioning, and a third level indicates excessively high elongation/tensioning of the waist elastic 125.

Means 131 for checking the elongation executed in accordance with the above description are especially appropriate for checking the elongation of the waist elastic in so-called panty diapers, where the waist elastic often extends around the entire waist opening of the panty diaper. The means 131 for checking elongation can be positioned in this case at any point on the waist elastic of the panty diaper. Positioning at the front on the abdomen area or at the rear on the back area is beneficial, however, having regard for the requirement that the means 131 must be easy to find and check after putting the panty diaper on a wearer.

Figure 1E:
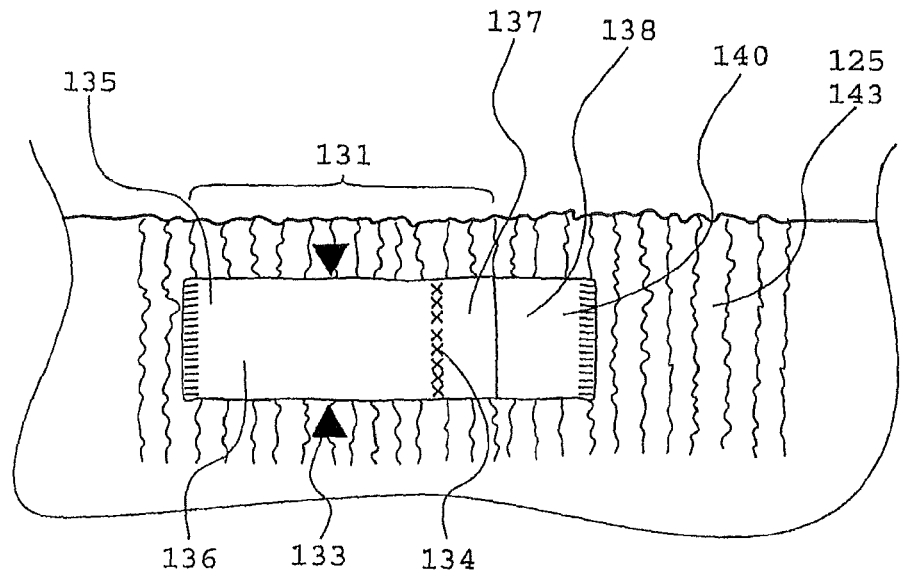
FIG. 1e is a schematic diagram that shows the waist elastic of the diaper in an alternative embodiment with associated means for checking the elongation of the elastic when the elastic is in the contracted state.
Figure 1F:
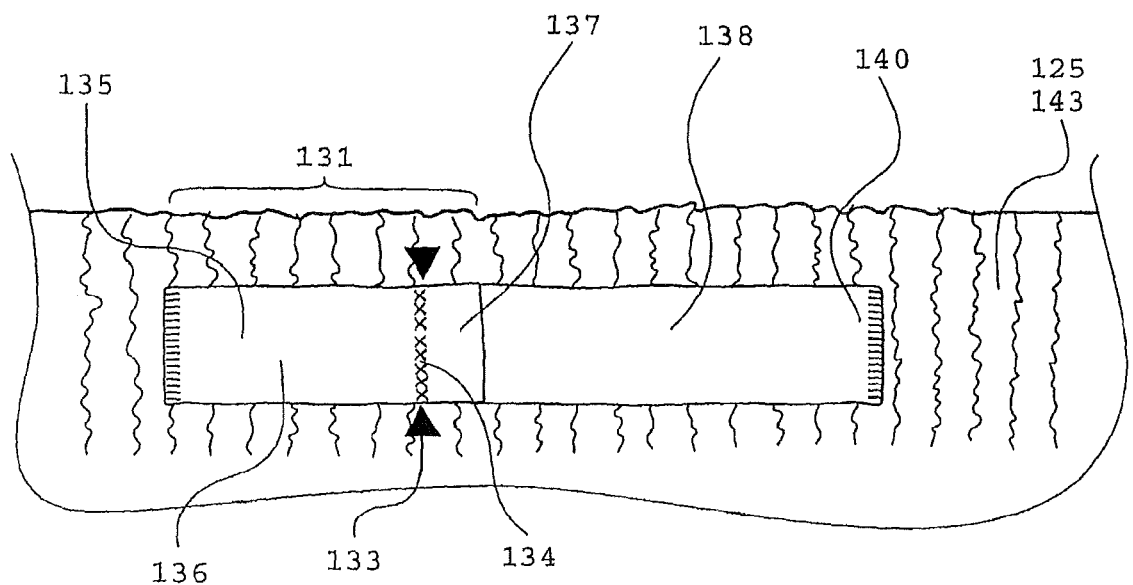
FIG. 1f is a schematic diagram that shows the waist elastic in FIG. 1e and the means for checking the elongation of the elastic in the stretched state.

Shown in FIGS. 1e and 1f is an alternative embodiment of the invention, whereby FIG. 1e shows the embodiment in the contracted state and FIG. 1f shows the embodiment when the waist elastic 125 is stretched.

The means 131 for checking the elongation of the waist elastic 125 comprises the same elements that are comprised in the means 131 described in the embodiment above. The means 131 for checking the elongation of the waist elastic 125 thus comprises an essentially inelastic piece of material 135, a first indicator marker 133 arranged on the elastic 125 and a second indicator marker 134 arranged on the piece of material 135. The piece of material 135 comprises, precisely as in the embodiment described above, a first end area 136 attached to the waist elastic 125 and a second end area 137.

The second end area 137 is attached to a rectangular, elastic piece of material 138, in conjunction with which the elastic piece of material 138 forms an extension of the essentially inelastic piece of material 135. The end area 140 of the elastic piece of material 138 is attached to the waist elastic 125.

When the part of the waist elastic 125 that is situated between the attachment of the essentially inelastic piece of material 135 to the backing layer 104 and the attachment of the elastic piece of material 138 to the backing layer 104 is extended, the whole of the extension must be taken up by the elastic piece of material 138 that is attached to the means 131 for checking the elastic elongation. Viewed in relative terms, the elastic piece of material 138 must, therefore, be elongated significantly more than the waist elastic 125, because the elastic piece of material 138 is significantly shorter than the distance between the attachment of the essentially inelastic piece of material 135 to the backing layer 104 and the attachment of the elastic piece of material 138 to the backing layer 104.

The elastic piece of material 138 is not necessary in order for the invention to function, although the introduction of the piece of material 138 means that the free end of the means 131 for checking the elastic elongation remains attached to the backing layer of the diaper 101 via the elastic piece of material 138.

The arrangement with the elastic piece of material 138 avoids the second end area 137 of the piece of material 135 being folded or coming out of position in some other way, which can jeopardize the function of the means 131 or present problems in conjunction with handling the diaper 101.

The diaper 101 is also characterized in that it exhibits a second means 132 for checking the elongation of the attachment flaps 126.

A first indicator marker 141 for indicating the elongation of the attachment flap 126 is arranged between the attachment area 130 of the respective elastic attachment flap 126 and the respective longitudinal edge 112,113 of the diaper 101. The indicator marker 141 consists of an area on the attachment flap 126 that is colored with a color that differs from the rest of the attachment flap 126. At least one part of the distance between the attachment area 130 of the attachment flap 126 and the indicator marker 141 must be elastic in order for the invention to be capable of functioning.

The second indicator marker 142 of the means 132 consists of the longitudinal edges 112,113 of the diaper 101, where these cross the respective attachment flap 126, in conjunction with which the backing layer 104 of the diaper 101 constitutes the essentially inelastic piece of material 145 on which the second indicator marker 142 is arranged.

The second indicator marker 142 is not specifically marked with any color or the like, but it can naturally be marked in an appropriate fashion in alternative embodiments.

Means 132 for indication are intended to indicate that the attachment flaps 126 are sufficiently tensioned, which they are when the second indicator marker 142 and the first indicator marker 141 are situated one on top of the other when the diaper 101 is put on a wearer.

In alternative embodiments, the first indicator marker 141 can comprise a number of levels, in conjunction with which, for example, a first level indicates incomplete stretching, an intermediate level indicates correct stretching, and a third level indicates excessive stretching of the attachment flap 126. The first level, which indicates incomplete stretching, is arranged in this case furthest from the attachment area 130 of the attachment flap 126, and the level which indicates excessive stretching is accordingly arranged nearest to the attachment area 130 of the attachment flap 126.

In other, alternative embodiments, the second indicator marker 142 of the means 132 can be arranged on the backing layer 104, in conjunction with which it is positioned, in the transverse direction of the diaper 101, between the first indicator marker 141 on the attachment flap 126 and the longitudinal edge of the diaper 101 when the attachment flap 126 is in its unstretched state. The indicator marker 142 can consist of a color marking, a glued-on label or the like. The second indicator marker 142 can also comprise various levels.

Figure 2A:
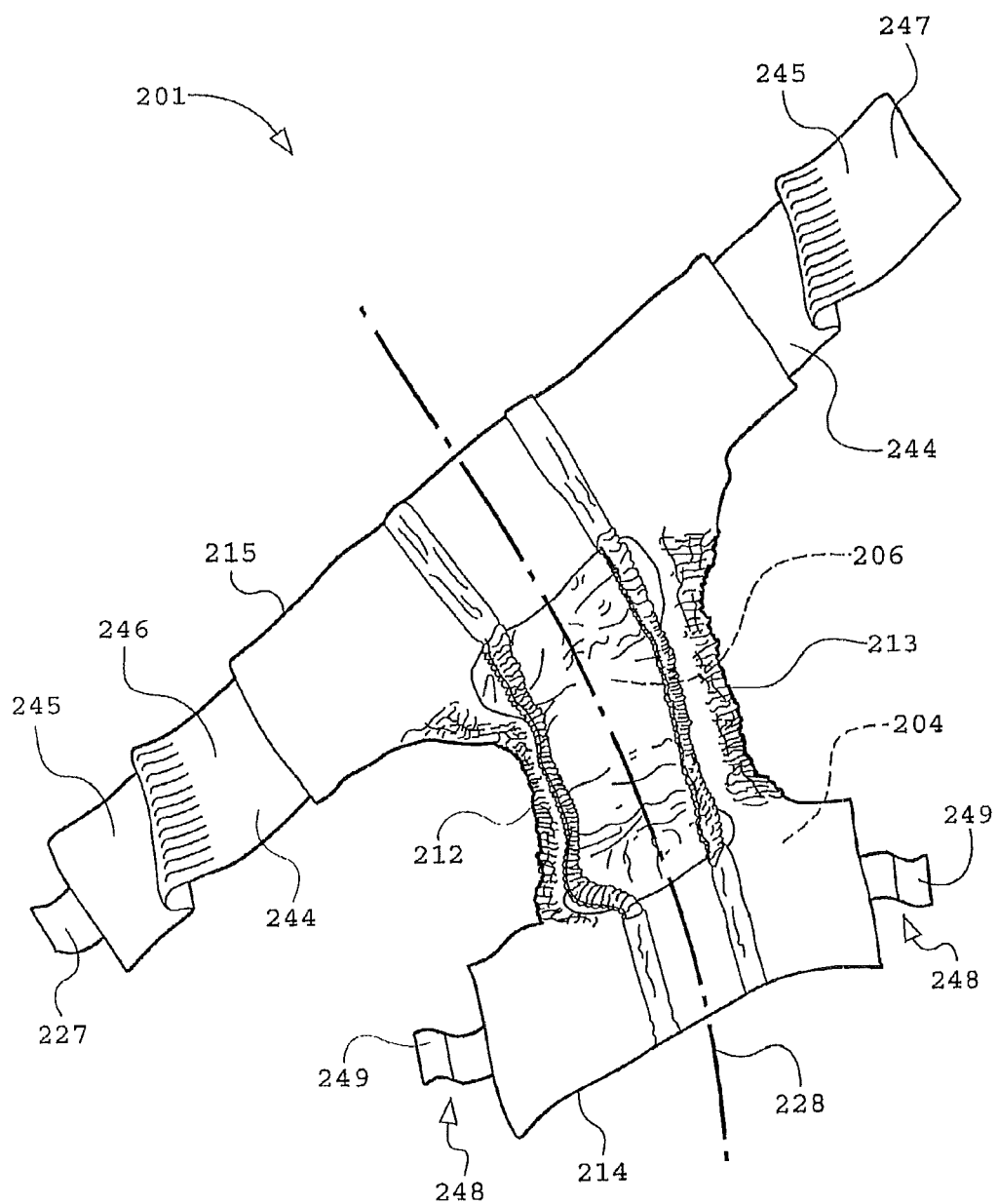
FIG. 2a shows a belt diaper in accordance with a second preferred embodiment of the invention from the side that is intended to face towards the wearer when wearing the diaper.
Figure 2B:
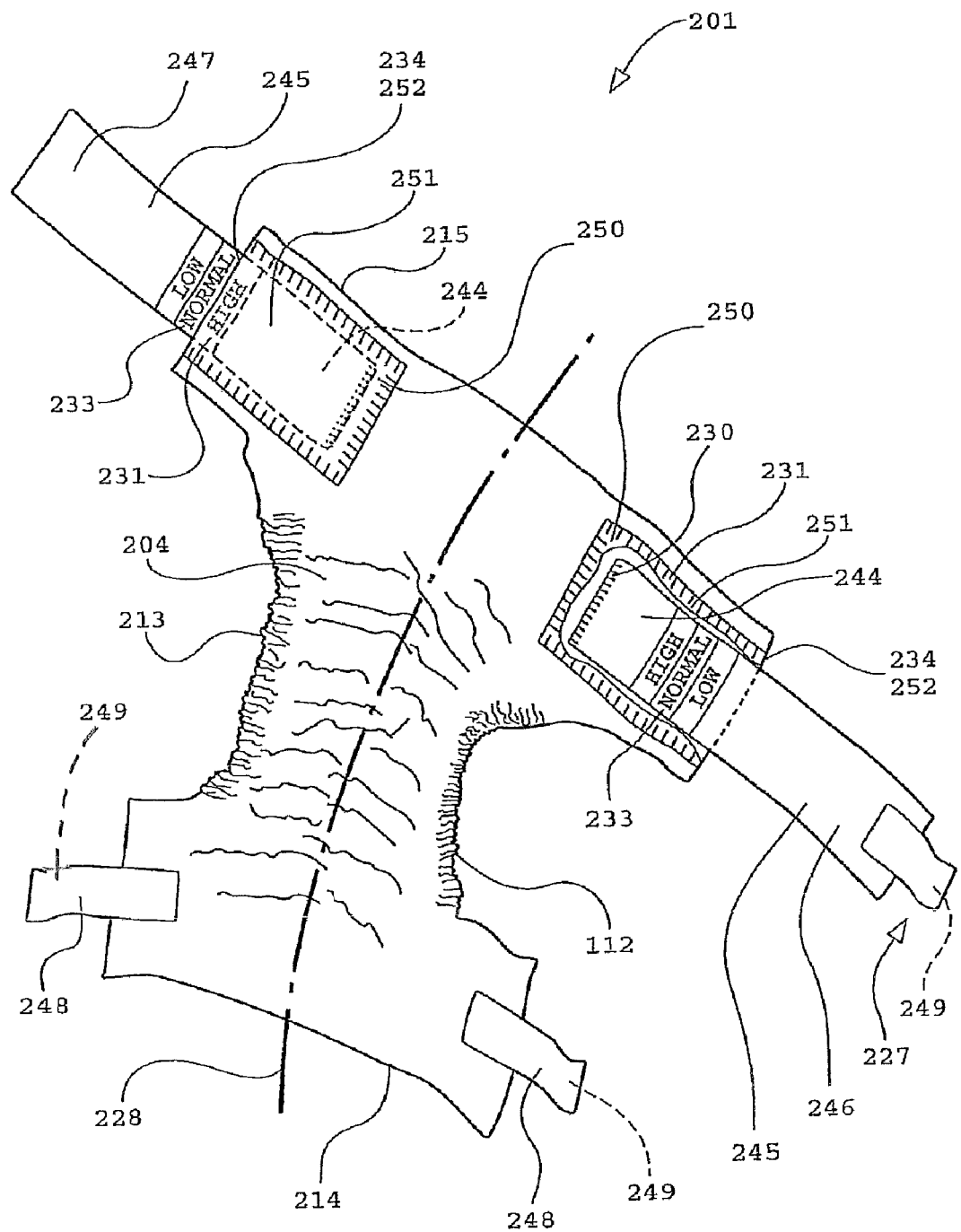
FIG. 2b shows the belt diaper in accordance with FIG. 2a from the side that is intended to face away from the wearer when wearing the diaper before it has been used.

FIG. 2a shows a belt diaper 201 in accordance with the invention from the side which, when it is being worn, is intended to face towards the wearer, and the same belt diaper 201 is shown from the opposite side in FIG. 2b.

The belt diaper 201 differs from an open diaper in that its attachment arrangement comprises an elastic belt 245 intended to enclose the wearer's waist, in conjunction with which the belt comprises a fixing device 227 for fixing the belt 245 around the wearer's waist.

The belt diaper 201 comprises two elastic belt halves 246, 247, in conjunction with which the respective half 246,247 of the belt is joined to the backing layer of the belt diaper 201 between the longitudinal edges 212, 213 of the belt diaper 201 and the longitudinal center line 228 next to the rear transverse edge 215.

The belt halves 246,247 extend in a transverse direction in relation to the absorption body 206 of the belt diaper 201.

The elastic belt halves 246,247 constitute examples of the elastic areas 244 of the belt diaper.

The attachment arrangement also comprises two front fixing devices 248 arranged on the longitudinal edges 212, 213 of the belt diaper 201 next to the front transverse edge 214. The front fixing devices 248 are intended to be fixed to the belt 245 in conjunction with putting the belt diaper 201 on a wearer.

The front fixing devices 248 comprise Velcro® elements 249 intended to interact with the side of the belt 245 that is intended to face away from the wearer when the diaper is being worn.

In alternative embodiments, the front fixing devices 248 can comprise adhesive elements intended to be fixed to the surface of the belt 245 facing away from the wearer. The belt 245 in this case must include surfaces intended to interact with the adhesive elements, for example surfaces which consist of a plastic film or the like.

When the belt diaper 201 is to be put on a wearer, the belt 245 is fixed around the wearer's waist as a first stage. The absorption part of the belt diaper 201 comprising, among other things, the front transverse edge 214 and the absorption body 206, is then passed between the wearer's legs, after which two front fixing devices 248 are finally attached to the side of the belt 245 facing away from the wearer.

The belt diaper 201 is characterized primarily in that it comprises means 231 for checking the elongation of the belt 245. Both belt halves 246,247 comprise means 231 for checking the elongation.

In order to illustrate more clearly how the means 231 for checking the elongation is constructed, a layer of material 250 which conceals the first indicator marker 233 of the means 231 when the belt is not subjected to any elongation has been removed in the case of one belt half 246 in FIG. 2b.

In order further to clarify the construction, the belt half 246 is shown in the non-elongated state, whereas the opposing belt half 247 is shown in a state in which it is extended to the normal level of use (this situation, with one belt half 246 not extended and with the other belt half 247 extended, is not in itself relevant in relation to wearing the diaper, but it is shown in this way for increased clarity).

The belt half 246,247 exhibits a first indicator marker 233 between the attachment area 230 of the belt half 246,247 and the longitudinal edge 212,213 of the belt diaper 201. The belt half 246,247 exhibits elasticity in at least one part of the area between the attachment area 230 and the first indicator marker 233.

The first indicator marker 233 comprises three fields arranged consecutively in the longitudinal direction of the belt half 246,247, in conjunction with which the fields indicate the levels "LOW", "NORMAL" and "HIGH". The field marked with the word "LOW" is arranged furthest away from the attachment 230 of the belt half 246,247 to the backing layer 204 and is intended to indicate that the belt has not been tightened sufficiently tightly around the wearer's waist. The field marked with the word "HIGH" is arranged closest to the attachment 230 of the belt half 246,247 to the backing layer 204 and is intended to indicate that the belt has been tightened too tightly around the wearer's waist. The field marked with the word "NORMAL" is arranged between the other two fields and indicates the correct tensioning of the belt around the wearer's waist.

The first indicator marker 233 in its entirety is concealed under the layer of material 250 when the belt half 246,247 is in its non-extended state.

The layer of material 250 is arranged on the backing layer 204, in conjunction with which it conceals the part of the belt half 246,247 that is situated between the attachment area 230 of the belt half 246,247 and the longitudinal edge 212,213 of the belt diaper 201. The layer of material 250 is attached to the backing layer 204 along three of its four edges outside the belt half 246,247, in conjunction with which the layer of material 250 forms one half of a pocket 251, and in conjunction with which the other half of the pocket 251 consists of the backing layer 204.

The pocket 251 is open along the edge where the belt half 246,247 projects.

The second indicator marker 234 of the means 231 consists of the free edge 252 of the layer of material 250, in conjunction with which the layer of material 250 constitutes the essentially inelastic piece of material of the means 231. The first indicator marker 233 of the means 231 is shown against the aforementioned edge 252 when the belt half 246,247 is stretched and one or other of the three levels of the first indicator marker 233 becomes visible on the aforementioned edge 252.

In alternative embodiments, the edge 252 of the layer of material 250 can be arranged inside or outside the longitudinal edge 212,213 of the belt diaper 201.

It is also possible to envisage embodiments in which the belt halves 246,247 are attached between the liquid-permeable covering layer 202 and the backing layer 204 of the belt diaper 201, in conjunction with which a pocket is arranged between the covering layers 202,204. The edge of the backing layer 204 where the belt half 246,247 projects from the belt diaper 201 forms the second indicator marker 234 of the means in such an embodiment.

In other alternative embodiments, the first indicator marker 233 can consist only of a line which runs across the belt half 246,247, in conjunction with which the line indicates only that the elongation of the belt is too high.

Belt diapers 201 can naturally be provided, in alternative embodiments, with the same type of means 132 that are described above for attachment flaps 126 for open, so-called all-in-one diapers 101.

The invention also extends to all conceivable combinations of the described illustrative embodiments.

Furthermore, the invention is not restricted to the above-mentioned illustrative embodiments, but is, of course, applicable to other embodiments within the scope of the following patent claims.

The invention having been described above with reference to certain specific embodiments thereof, it will be recognized that these embodiments do not limit the scope of the appended claims.

The invention claimed is:

1. An absorbent article comprising:
   an absorption body;
   an elastic area arranged outside of the absorption body and having a direction of elongation;
   a checking device for checking the elongation of the elastic area, the checking device comprising:
   a first indicator marker connected to the elastic area, and
   a second indicator marker connected to an inelastic second piece of material such that the first indicator marker and the second indicator marker are capable of displacement relative to one another by a distance in the direction of elongation of the elastic area,
   whereby a change in the relative position between the first and the second indicator marker in conjunction with elongation of the elastic area from a non-elongated position to an elongated position provides a measure of elongation of the elastic area.

2. The absorbent article, as claimed in claim 1, wherein the first indicator marker is displaced in the direction of elongation when the elastic area is elongated, as a consequence of which it is displaced for a greater distance than the second indicator marker.

3. The absorbent article, as claimed in claim 1, wherein elongation of the elastic area reduces the distance between the first indicator marker and the second indicator marker.

4. The absorbent article, as claimed in claim 1, wherein the second piece of material comprising the second indicator marker is attached at a first end area to the elastic area along an attachment line essentially perpendicular to the direction of elongation of the elastic area, and the second indicator marker is arranged at a distance from the attachment line in the direction of elongation of the elastic area, the second indicator marker being proximal a second end area of the second piece of material, the second end area being unattached to the elastic area.

5. The absorbent article, as claimed in claim 4, wherein the second indicator marker comprises one edge of the second piece of material, and the one edge is arranged at a distance from the attachment line of the piece of material essentially perpendicular to the direction of elongation of the elastic area.

6. The absorbent article, as claimed in claim 1, wherein the first indicator marker is concealed under the second piece of material when the elastic area is not stretched.

7. The absorbent article, as claimed in claim 1, wherein the first indicator marker comprises at least two indicator levels, at least one of the indicator levels indicates that the elastic area has been stretched too much.

8. The absorbent article, as claimed in claim 7, wherein another of the indicator levels indicates that the elastic area of the article is not sufficiently stretched to ensure the satisfactory function of the article.

9. The absorbent article, as claimed in claim 1, wherein the article is a panty diaper.

10. The absorbent article, as claimed in claim 9, wherein the elastic area comprises waist elastic of the panty diaper.

11. The absorbent article, as claimed in claim 1, wherein the article is an all-in-one diaper.

12. The absorbent article, as claimed in claim 11, wherein the elastic area comprises at least a part of an attachment flap of the all-in-one diaper.

13. The absorbent article, as claimed in claim 12, wherein the attachment flap is attached to a backing layer of the all-in-one diaper between a longitudinal edge and a longitudinal center line of the diaper, and the first indicator marker is arranged on the attachment flap between the attachment and the longitudinal edge, at least one part of the attachment flap between the attachment and the first indicator marker is elastic, and the second indicator marker is arranged on the backing layer and positioned in the transverse direction of the article between the first indicator marker and the longitudinal edge, and the backing layer constitutes the second piece of material.

14. The absorbent article, as claimed in claim 13, wherein the second indicator marker comprises the longitudinal edge of the all-in-one diaper.

15. The absorbent article, as claimed in claim 13, wherein at least one part of the attachment flap between its attachment to the backing layer and the longitudinal edge of the all-in-one diaper is concealed under the second piece of material.

16. The absorbent article, as claimed in claim 15, wherein the second piece of material forms a pocket together with the backing layer, wherein the pocket is open where the attachment flap extends outwards from the pocket, and the attachment between the attachment flap and the backing layer is arranged inside the pocket.

17. The absorbent article, as claimed in claim 11, wherein the elastic area comprises a waist elastic of the all-in-one diaper.

18. The absorbent article, as claimed in claim 1, the article is a belt diaper.

19. The absorbent article, as claimed in claim 18, wherein the elastic area comprises at least one part of at least one of the belt halves of the belt diaper.

20. The absorbent article, as claimed in claim 19, wherein the belt half is attached to a backing layer of the belt diaper between a longitudinal edge and a longitudinal center line of the diaper, the first indicator marker is arranged on the belt half between the attachment and the longitudinal edge, at least a part of the belt half between the attachment and the first indicator marker is elastic, and the second indicator marker is arranged on the backing layer and positioned in the transverse direction of the article between the first indicator marker and the longitudinal edge, and the backing layer constitutes the second piece of material.

21. The absorbent article, as claimed in claim 20, wherein the second indicator marker comprises the longitudinal edge of the belt diaper.

22. The absorbent article, as claimed in claim 21, wherein the belt halves are arranged between a liquid-permeable covering layer and the backing layer.

23. The absorbent article, as claimed in claim 18, wherein at least one part of the extent of the belt half between its attachment to the backing layer and the longitudinal edge of the belt diaper is concealed under the second piece of material.

24. The absorbent article, as claimed in claim 22, wherein the second piece of material forms a pocket together with the backing layer, the pocket is open where the belt half extends outwards from the pocket, and the attachment between the belt half and the backing layer is arranged inside the pocket.

* * * * *